US012675147B2

(12) United States Patent
Kokovidis et al.

(10) Patent No.: US 12,675,147 B2
(45) Date of Patent: *Jul. 7, 2026

(54) AUTOMATIC POWER ON APPARATUS, SYSTEM, METHOD, AND CIRCUIT

(71) Applicant: Drägerwerk AG & Co. KGaA, Lübeck (DE)

(72) Inventors: Georgios Kokovidis, Waltham, MA (US); Peter Andrew Lund, Nashua, NH (US)

(73) Assignee: Drägerwerk AG & Co. KGaA, Lübeck (DE)

( * ) Notice: Subject to any disclaimer, the term of this patent is extended or adjusted under 35 U.S.C. 154(b) by 15 days.

This patent is subject to a terminal disclaimer.

(21) Appl. No.: 18/924,404

(22) Filed: Oct. 23, 2024

(65) Prior Publication Data

US 2025/0044852 A1 Feb. 6, 2025

Related U.S. Application Data

(63) Continuation of application No. 17/789,083, filed as application No. PCT/IB2020/062364 on Dec. 22, 2020, now Pat. No. 12,158,788.

(60) Provisional application No. 62/953,662, filed on Dec. 26, 2019.

(51) Int. Cl.
*G06F 1/3203* (2019.01)
*A61B 5/00* (2006.01)
*G16H 40/67* (2018.01)

(52) U.S. Cl.
CPC ............ *G06F 1/3203* (2013.01); *A61B 5/002* (2013.01); *G16H 40/67* (2018.01)

(58) Field of Classification Search
None
See application file for complete search history.

(56) References Cited

U.S. PATENT DOCUMENTS

| | | | | |
|---|---|---|---|---|
| 12,158,788 B2* | 12/2024 | Kokovidis | ............. | G16H 40/63 |
| 2013/0236192 A1* | 9/2013 | Deicke | .................... | H02J 7/485 |
| | | | | 398/135 |
| 2014/0184516 A1* | 7/2014 | Kim | ....................... | G06F 3/0231 |
| | | | | 345/169 |
| 2016/0129182 A1* | 5/2016 | Schuster | ............. | A61M 15/008 |
| | | | | 702/56 |

* cited by examiner

*Primary Examiner* — Thomas S McCormack
(74) *Attorney, Agent, or Firm* — Nolte Lackenbach Siegel

(57) ABSTRACT

An automatic power on apparatus, system, method, and circuit automatically control the on/off state of a first electronic device or a second electronic device. When the second electronic device is positioned on, in, or proximate to the mounting area of the first electronic device, the automatic power on circuit establishes a coupling signal between a first portion of the automatic power on circuit and a second portion of the automatic power on circuit, activates the automatic power on circuit based on the coupling signal, and automatically controls an on/off state of the first electronic device or the second electronic device based on the activation of the automatic power on circuit.

19 Claims, 9 Drawing Sheets

AUTOMATIC POWER ON APPARATUS, SYSTEM, METHOD, AND CIRCUIT

FIELD

The subject matter of the present disclosure relates generally to the use of an automatic power on circuit to control the on and off states of medical devices used in, for example, a patient care or a hospital environment.

BACKGROUND

Currently, there is no way to seamlessly and automatically control the on/off states of medical devices. For example, there is no way to seamlessly and automatically transition from monitoring a patient from a smaller transportable medical device to a larger medical device (e.g., a stationary medical device) or from a larger medical device to a smaller transportable medical device, particularly if either the smaller transportable medical device or the larger medical device is turned off or in a sleep mode.

Specifically, when a patient is being transported between different patient care or hospital environments, clinicians are required to perform manual operations when transitioning between different medical devices (e.g., attaching cables or pushing of buttons on the front panel of the smaller transportable medical device or the larger medical device). This manual action increases workload on clinicians and increases the overall time for performing accurate patient assessment.

Thus, it would be advantageous and an improvement over the relevant technology to provide an automatic power on apparatus, system, method, and circuit that seamlessly and automatically control the on/off states of medical devices in a way that reduces workload on clinicians and supports rapid patient assessment.

SUMMARY

An embodiment described in the present disclosure provides an automatic power on system including a first electronic device including, a mounting area on a surface and a first portion of an automatic power on circuit; and a second electronic device including a size and shape so as to be positioned on, in, or proximate to the mounting area of the first electronic device, and including a second portion of an automatic power on circuit.

With this embodiment, when the second electronic device is positioned on, in, or proximate to the mounting area of the first electronic device, the automatic power on circuit is configured to establish a coupling signal between the first portion of the automatic power on circuit and the second portion of the automatic power on circuit, activate the automatic power on circuit based on the coupling signal, and automatically control an on/off state of the first electronic device or the second electronic device based on the activation of the automatic power on circuit.

For example, upon the activation of the automatic power on circuit, the first electronic device is controlled to turn on so as to match the on state of the second electronic device. In the alternative, the second electronic device is controlled to turn on so as to match the on state of the first electronic device. However, when the first electronic device is in an on/off state that matches the on/off state of the second electronic device prior to activation of the automatic power on circuit, the first electronic device remains in a same on/off state after activation of the automatic power on circuit.

Similarly, when the second electronic device is in an on/off state that matches the on/off state of the first electronic device prior to activation of the automatic power on circuit, the second electronic device remains in a same on/off state after activation of the automatic power on circuit.

An embodiment described in the present disclosure provides an automatic power on method for a system that includes positioning the second electronic device on, in, or proximate to a mounting area on a surface of the first electronic device, establishing a coupling signal between the first portion of the automatic power on circuit and the second portion of the automatic power on circuit, activating the automatic power on circuit based on the coupling signal, and automatically controlling an on/off state of the first electronic device or the second electronic device based on the activation of the automatic power on circuit.

An embodiment described in the present disclosure provides an automatic power on circuit that includes a first portion of an automatic power on circuit configured within a first electronic device, and a second portion of the automatic power on circuit configured within a second electronic device.

In an embodiment of the present disclosure, the automatic on/off circuit is a phototransistor circuit that establishes a coupling connection between the second portion of the automatic on/off circuit and the first portion of the automatic on/off circuit using an infrared (IR) light emitting diode (LED) and a phototransistor. However, it is also contemplated by the present disclosure that the automatic power on circuit could be modified to establish a coupling signal between the second portion of the automatic on/off circuit and the first portion of the automatic on/off circuit using other wireless circuit configurations that use radio frequency, near-field magnetic induction (NFMI), Bluetooth, or WiFi.

An embodiment described in the present disclosure provides a first electronic device for wirelessly coupling with a second electronic device having a second portion of an automatic on/off circuit. The first electronic device is of a size and shape so as to be positioned on, in, or proximate to a mounting area of the second electronic device, and includes a first portion of the automatic on/off circuit.

When the first electronic device is positioned on, in, or proximate to the mounting area of the second electronic device, the first portion of the automatic power on circuit is configured to establish a coupling signal between the first portion of the automatic power on circuit and the second portion of the automatic power on circuit, activate the automatic power on circuit based on the coupling signal, and automatically control an on/off state of the second electronic device based on the activation of the automatic power on circuit.

BRIEF DESCRIPTION OF THE DRAWINGS

In the drawings, like reference numbers generally indicate identical, functionally similar, and/or structurally similar elements.

DETAILED DESCRIPTION

Figure 1:
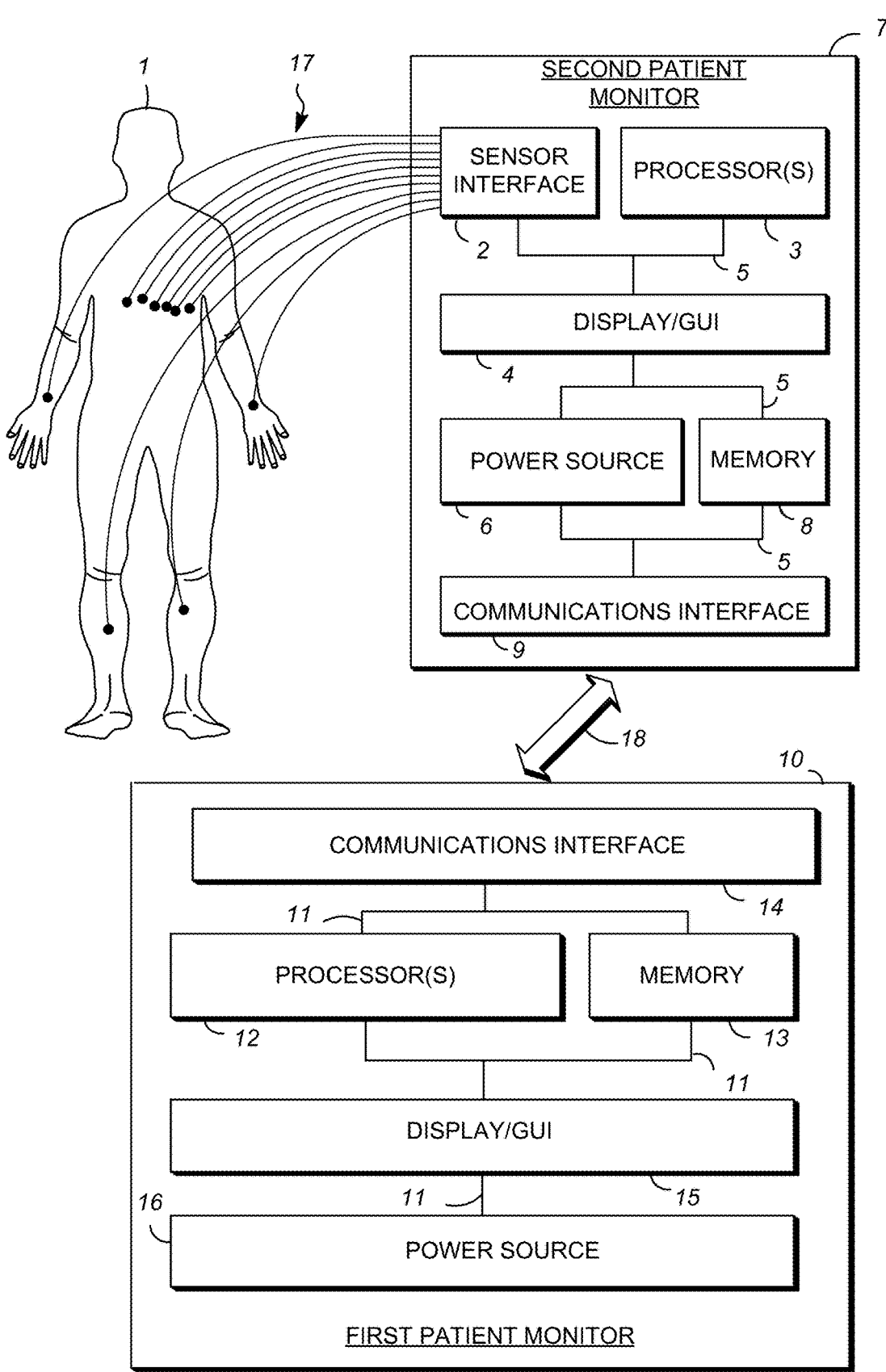
FIG. 1 is a schematic diagram of an automatic power on system according to one or more embodiments of the present disclosure.

The following detailed description is made with reference to the accompanying drawings and is provided to assist in a comprehensive understanding of various example embodiments of the present disclosure. The following description includes various details to assist in that understanding, but these are to be regarded as merely examples. Accordingly, those of ordinary skill in the art will recognize that various changes and modifications of the examples described herein can be made without departing from the spirit and scope of the present disclosure. In addition, descriptions of well-known functions and constructions may be omitted for clarity and conciseness.

For example, in the description of the figures that follow, the automatic power on apparatus, system, method, and circuit are implemented in patient monitors. However, it should be understood and appreciated by one of ordinary skill in the art that the automatic power on apparatus, system, method, and circuit of the present disclosure can be implemented in other medical or electronic devices. The implementation of the automatic power on apparatus, system, method, and circuit in the patient monitors is meant only to assist in the understanding of the present disclosure and in no way is meant to limit the implementation the automatic power on apparatus, system, method, and circuit described herein.

Additionally, the terms and words used in the following description and claims are not limited to the bibliographical meanings, but are merely used to enable a clear and consistent understanding of the present disclosure. Accordingly, it should be apparent to those skilled in the art that the following description of the present disclosure is provided for illustration purposes only, and not for the purpose of limiting the present disclosure as defined by the appended claims and their equivalents.

Features from different embodiments may be combined to form further embodiments, unless specifically noted otherwise. Variations or modifications described with respect to one of the embodiments may also be applicable to other embodiments. In some instances, well-known structures and devices are shown in block diagram form rather than in detail in order to avoid obscuring the embodiments.

Further, equivalent or like elements or elements with equivalent or like functionality are denoted in the following description with equivalent or like reference numerals. As the same or functionally equivalent elements are given the same reference numbers in the figures, a repeated description for elements provided with the same reference numbers may be omitted. Hence, descriptions provided for elements having the same or like reference numbers are mutually exchangeable.

The term "substantially" may be used herein to account for small manufacturing tolerances (e.g., within 5%) that are deemed acceptable in the industry without departing from the aspects of the embodiments described herein.

In the present disclosure, expressions including ordinal numbers, such as "first", "second", and/or the like, may modify various elements. However, such elements are not limited by the above expressions. For example, the above expressions do not limit the sequence and/or importance of the elements. The above expressions are used merely for the purpose of distinguishing an element from the other elements. For example, a first box and a second box indicate different boxes, although both are boxes. For further example, a first element could be termed a second element, and similarly, a second element could also be termed a first element without departing from the scope of the present disclosure.

FIG. 1 is a schematic diagram of an automatic power on system implemented in medical devices such as patient monitors according to an embodiment of the present disclosure implemented. As shown in FIG. 1, the automatic power on system includes a first patient monitor 10 and a second patient monitor 7 that are connectable. In particular, the second patient monitor 7 may be docked with, mounted to, or brought in proximity to the first patient monitor 10, thereby establishing one or more connections, and may be further undocked with, unmounted from, or brought out of proximity to the first patient monitor 10, thereby disengaging the one or more connections.

Connections include in some cases wired connections, wireless connections, or a combination thereof. Connections may also include communication connections, data connections, signal connections, power connections, optical connections (optical couplings), electrical connections (electrical couplings), capacitive connections (capacitive couplings), inductive connections (inductive couplings), magnetic connections (magnetic couplings), radio frequency (RF) connections (RF couplings), or any combination thereof. Proximity as defined herein is to be within a range or distance that enables a coupling between devices sufficient to establish a coupling signal therebetween, where a coupling can be any coupling including electrical, optical, capacitive, inductive, magnetic, RF, or any other type of signal coupling.

The second patient monitor 7 is capable of receiving signals or data associated with physiological parameters from various physiological sensors 17 connected to a patient 1. The first patient monitor 10 is connected to the second patient monitor 7 through at least a communication connection 18. The second patient monitor 7 is, for example, a portable physiological patient monitor that can be transported with the patient 1 when being transported between different patient care and hospital areas. The second patient monitor 7 has a shape and/or a size that differs (e.g., smaller) from that of the first patient monitor 10. The first patient monitor 10 is, for example, a larger stationary patient monitor located in the patient care or hospital area or a portable patient monitor.

It is contemplated by the present disclosure that the second patient monitor 7 and the first patient monitor 10 include electronic components or electronic computing devices capable to receive, transmit, process, store, and/or manage patient data and information associated with performing the functions of the system, which encompasses any suitable processing device adapted to perform computing tasks consistent with the execution of computer-readable instructions stored in a memory or a computer-readable recording medium.

Further, any, all, or some of the computing devices in the second patient monitor 7 and the first patient monitor 10 may be adapted to execute any operating system, including Linux, UNIX, Windows, MacOS, DOS, and ChromOS, as well as virtual machines adapted to virtualize execution of a particular operating system, including customized and proprietary operating systems. The second patient monitor 7 and the first patient monitor 10 are further equipped with components to facilitate communication with other computing devices over one or more network connections, which may include connections to local and wide area networks, wireless and wired networks, public and private networks, and any other communication network enabling communication in the system.

As shown in FIG. 1, the second patient monitor 7 includes a sensor interface 2, one or more processors 3, a display/graphical user interface (GUI) 4, a memory 8, a power source 6, and a communications interface 9. The sensor interface 2 can be implemented in software or hardware and be used to connect via wired and/or wireless connections to one or more physiological sensors 17 and/or medical devices (e.g., electrocardiogram (ECG) electrodes, oxygen saturation (SpO2) sensors, blood pressure cuffs, apnea detection sensors, or respirators) for gathering physiological data from the patient 1.

The data signals from the physiological sensors 17 include, for example, data related to an electrocardiogram (ECG), non-invasive peripheral SpO2, non-invasive blood pressure (NIBP), temperature, and/or end-tidal carbon dioxide (etCO2), apnea detection, and other similar physiological data. The one or more processors 3 are used for controlling the general operations of the second patient monitor 7. Each one of the one or more processors 3 can be, but are not limited to, a central processing unit (CPU), a hardware microprocessor, a multi-core processor, a single core processor, a field programmable gate array (FPGA), a microcontroller, an application specific integrated circuit (ASIC), a digital signal processor (DSP), or other similar processing device capable of executing any type of instructions, algorithms, or software for controlling the operation and performing the functions of the second patient monitor 7.

The display/GUI 4 is configured for displaying various patient data and hospital or patient care information and includes a user interface implemented for allowing communication between a user and the second patient monitor 7. The display/GUI 4 includes, but is not limited to, a keyboard, a liquid crystal display (LCD), cathode ray tube (CRT), thin film transistor (TFT), light-emitting diode (LED), high definition (HD) or other similar display device including a display device having touch screen capabilities. The patient information displayed can, for example, relate to the measured physiological parameters of the patient 1 (e.g., blood pressure, heart related information, pulse oximetry, respiration information, and body temperature) that may be received or derived from one or more physiological sensors 17 as well as information related to the transporting of the patient 1 (e.g., transport indicators).

The memory 8 can be a single memory or one or more memories or memory locations that include, but are not limited to, a random access memory (RAM), dynamic random access memory (DRAM) a memory buffer, a hard drive, a database, an erasable programmable read only memory (EPROM), an electrically erasable programmable read only memory (EEPROM), a read only memory (ROM), a flash memory, hard disk or any other various layers of memory hierarchy. The memory 8 can be used to store any type of instructions and patient data associated with algorithms, processes, or operations for controlling the general functions and operations of the second patient monitor 7.

The power source 6 provides power to the second patient monitor 7 and its components, and can include a self-contained power source such as a battery pack and an interface to be powered through an electrical outlet (e.g., either directly or by way of another patient monitor) or other external power source. The power source 6 can also include a rechargeable battery that can be detached allowing for replacement. In the case of a rechargeable battery, a small built-in back-up battery (e.g., a super capacitor) can be provided for continuous power to be provided to the second patient monitor 7 during battery replacement. Additionally, the power source 6 includes switching circuitry (e.g., an on/off controller or power state controller) for an on/off switch for turning on and off the power from the power source 6 to the components of the second patient monitor 7. Communication between the components of the second patient monitor 7 (e.g., 2, 3, 4, 6, 8, and 9) is accomplished using an internal bus 5. Thus, the second patient monitor 7 includes a controller that controls the routing of power from the power source 6, the routing of power from an external power source, routing of power from a back-up battery, and a recharging of the power source 6 in the case it is a rechargeable battery. These functions may be performed by a power control circuit (not illustrated) that includes the on/off controller or power state controller.

The communications interface 9 allows the second patient monitor 7 to directly communicate with the first patient monitor 10 by establishing a communication connection 18 with the communications interface 14 of the first patient monitor 10 when the second patient monitor 7 is positioned in, on, or proximate to the first patient monitor 10. The communications interfaces 9, 14 of both monitors 7, 10 can include various network cards, interfaces, and circuitry to enable wireless communications between the second patient monitor 7 and the first patient monitor 10.

Additionally, the communications interfaces 9, 14 include a portion (e.g., first portion or second portion) of an automatic on/off circuit that establishes the communication connection 18. That is, when the second patient monitor 7 is positioned on, in, or proximate to the first patient monitor 10, the automatic power on circuit is configured to establish a coupling signal and a communication connection 18 between the first portion of the automatic power on circuit and the second portion of the automatic power on circuit. The operation of an example automatic on/off circuit for establishing the communication connection 18 between the first patient monitor 10 and the second patient monitor 7 will be discussed in more detail with reference to FIGS. 2A and 2B.

The communication connection 18 established by the communications interfaces 9, 14 includes, but is not limited to, an infrared (IR) connection, a radio frequency connection, a near-field magnetic induction (NFMI) connection, a Bluetooth connection, or a WiFi connection. Other wireless communication connections implemented using the communications interfaces 9, 14 may also include wireless connections that operate in accordance with, but are not limited to, IEEE802.11 protocol, a Radio Frequency For Consumer Electronics (RF4CE) protocol, ZigBee protocol, or IEEE802.15.4 protocol. The communications interfaces 9, 14 can also include circuitry to enable direct device-to-device connection to other devices such as to a tablet, PC, or similar electronic device; or to an external storage device or memory.

As shown in FIG. 1, the first patient monitor 10 includes one or more processors 12, a memory 13, a display/GUI 15, and a power source 16. The one or more processors 12 are used for controlling the general operations of first patient monitor 10. Each one of the one or more processors 12 can be, but are not limited to, a central processing unit (CPU), a hardware microprocessor, a multi-core processor, a single core processor, a field programmable gate array (FPGA), a microcontroller, an application specific integrated circuit (ASIC), a digital signal processor (DSP), or other similar processing device capable of executing any type of instructions, algorithms, or software for controlling the operation and performing the functions of the first patient monitor 10.

The memory 13 can be a single memory or one or more memories or memory locations that include, but are not limited to a random access memory (RAM), a dynamic random access memory (DRAM), a memory buffer, a hard drive, a database, an erasable programmable read only memory (EPROM), an electrically erasable programmable read only memory (EEPROM), a read only memory (ROM), a flash memory, hard disk or any other various layers of memory hierarchy. The memory 13 can be used to store any type of instructions associated with algorithms, processes, or operations for controlling the general functions and operations of the first patient monitor 10.

The display/GUI 15 includes, but is not limited to, a keyboard, a liquid crystal display (LCD), cathode ray tube (CRT), thin film transistor (TFT), light-emitting diode (LED), high definition (HD) or other similar display device including a display device with touch screen capabilities. The patient information displayed can, for example, relate to the measured physiological parameters of the patient 1 (e.g., blood pressure, heart related information, pulse oximetry, respiration information, and body temperature) as well as information related to the transporting of the patient 1 (e.g., transport indicators).

The power source 16 can include a self-contained power source such as a battery pack and an interface to be powered through an electrical outlet (e.g., either directly or by way of another patient monitor) or other power source. The power source 16 can include a rechargeable battery that can be detached allowing for replacement. In the case of a rechargeable battery, a small built-in back-up battery (e.g., a super capacitor) can be provided for continuous power to be provided to the first patient monitor 10 during battery replacement. Additionally, the power source 16 includes switching circuitry for an on/off switch for turning on and off the power from the power source 16 to the components of the first patient monitor 10. Communication between the components of the first patient monitor (e.g., 12, 13, 14, 15 and 16) is established using an internal bus 11. Thus, the first patient monitor 10 may include a controller that controls the routing of power from the power source 16 to the second patient monitor 7 (i.e., to the power source 6), the routing of power from an external power source, routing of power from a back-up battery, and a recharging of the power source 16 in the case it is a rechargeable battery. These functions may be performed by a power control circuit (not illustrated) that includes the on/off controller or power state controller.

Figure 2A:
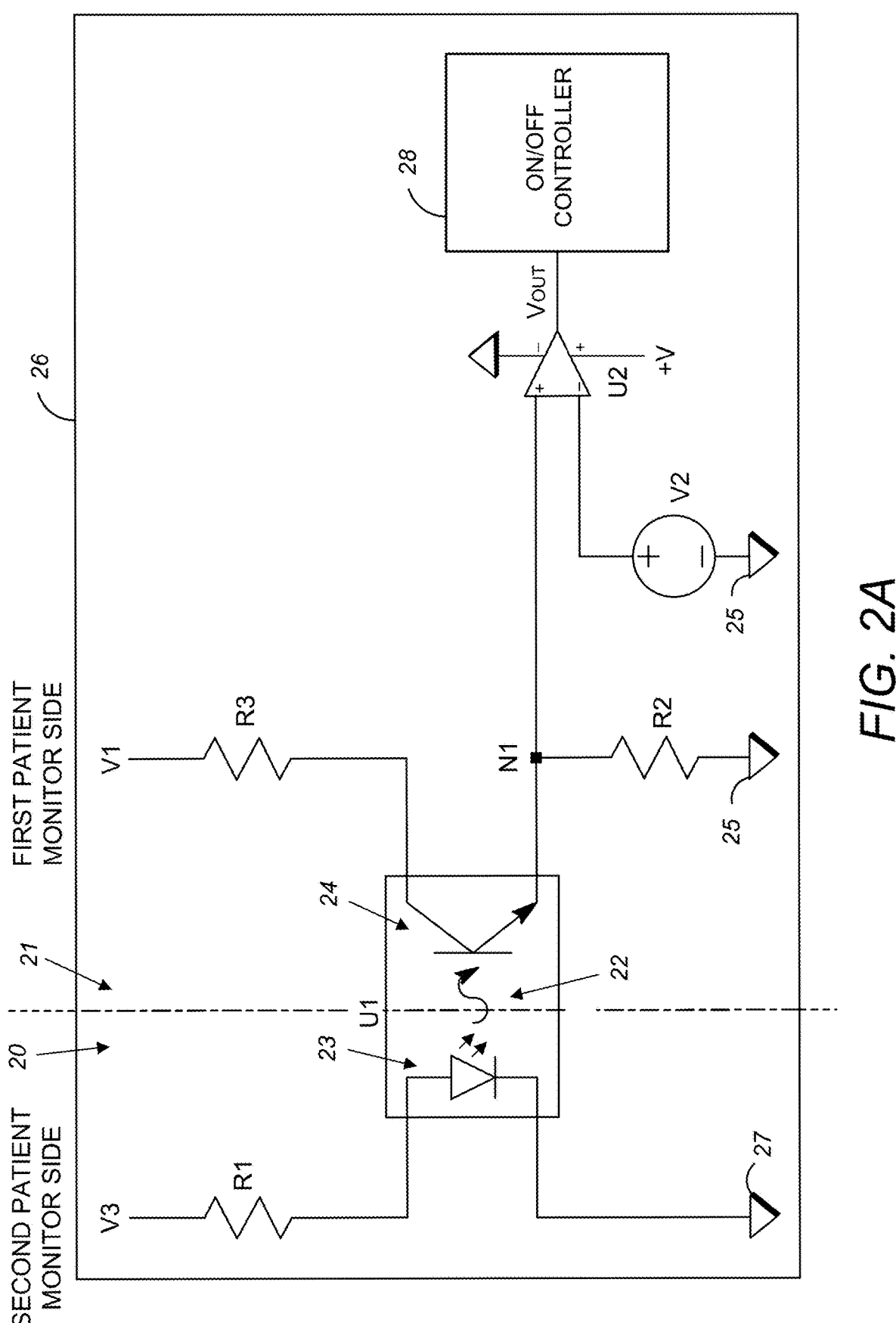
FIG. 2A is a schematic diagram of an automatic power on circuit according to one or more embodiments of the present disclosure.

FIG. 2A is a schematic diagram of an automatic power on circuit according to an embodiment of the present disclosure.

As shown in FIG. 2A, the automatic on/off circuit 26 includes a phototransistor circuit U1 that establishes a coupling connection 22 (e.g., coupling signal) between a portion of the automatic on/off circuit 20 on the second patient monitor side provided at the second patient monitor 7 (e.g., a communications interface 9) and a portion of the automatic on/off circuit 21 on the first patient monitor side provided at the first patient monitor 10 (e.g., a communications interface 14). The portion of the automatic on/off circuit 20 includes an infrared (IR) light emitting diode (LED) 23 or other light source and the portion of the automatic on/off circuit 21 includes a phototransistor 24 or other photodetector that generates an electrical signal representative of received light. However, it is also contemplated by the present disclosure that the automatic power on circuit may be modified to establish a coupling signal between the different portions of the automatic power on circuit using radio frequency, near-field magnetic induction (NFMI), Bluetooth, or WiFi.

The portion of the automatic on/off circuit 20 is provided, for example, in the communications interface 9 of the second patient monitor 7 and receives power from the power source 6 through the internal bus 5. The portion of the automatic on/off circuit 21 is provided, for example, in the communications interface 14 of the first patient monitor 10 and receives power from the power source 16 through the internal bus 11.

In FIG. 2A, it is assumed that the second patient monitor 7 has been positioned on, in, or proximate to the first patient monitor 10, such that a coupling signal 22 can be established between the portion of the automatic power on circuit 20 and the portion of the automatic power on circuit 21. Example configurations of the second patient monitor 7 positioned on, in, or proximate to the first patient monitor 10 for establishing the coupling signal 22 are discussed in more detail with reference to FIGS. 3, 5, 6A, and 6B.

Additionally, in FIG. 2A, it is assumed that the power source 6 of the second patient monitor 7 is turned on and is providing power to the components of the second patient monitor 7, including the portion of the automatic on/off circuit 20 on the second monitor side, as indicated by the voltage V3. The portion of automatic on/off circuit 20 is also attached to ground 27 so that the applied voltage V3 causes a current to flow through resistor R1 and IR LED 23 of the phototransistor circuit U1. The current flowing through the IR LED 23 causes the IR LED 23 to emit IR light as a coupling signal 22 toward the phototransistor 24 of the phototransistor circuit U1. V3 may be a DC voltage with a pre-determined voltage level (e.g., +3.3 V), and the generated current flowing through the IR LED 23 may be constant. Alternatively, V3 may be a switched power supply that provides programmable pulses to the IR LED 23, and the generated current is pulsed.

The portion of the automatic on/off circuit 21 is attached to ground 25 so that the light received by the phototransistor 24 activates the phototransistor 24 and causes current to flow through phototransistor 24 from the voltage V1 applied to the resistor R3. The voltage V1 is supplied from a connection to the power source 16 through the internal bus 11 of the first patient monitor 10.

The current flowing through the phototransistor 24 turns on an output of the comparator U2, which produces a voltage Vout from the portion of the automatic on/off circuit 21. Specifically, voltage Vout is generated by the comparator U2 when the voltage at node N1 exceeds the voltage of V2. Otherwise, the comparator U2 outputs 0V. The voltage Vout from the portion of the automatic on/off circuit 21 is provided to the switching circuitry for the on/off switch of the power source 16 of the first patient monitor 10 through the internal bus 11, which automatically turns on the first patient monitor 10 when the first patient monitor 10 is turned off or in a sleep mode.

In particular, the automatic on/off circuit 26 includes an on/off controller 28 that is connected to the output of the comparator U2 for receiving the control voltage Vout. The on/off controller 28 is configured to turn on and off power supplied from the power source 16 of the first patient monitor 10 based on the output of the comparator U2. For example, when the output of the comparator U2 is equal to Vout and the on/off controller 28 is in the off state or a sleep mode state, the on/off controller 28 is configured to turn on the power supply from the power source 16 such that components of the first patient monitor 10 receive power therefrom. When the output of the comparator U2 is equal to Vout and the on/off controller 28 is already in the on state, the on/off controller 28 is configured to maintain the on state from the power supply. In other words, when the on/off controller 28 is already in the on state, the output of the comparator U2 can be ignored.

As alluded to above, the on/off controller 28 may not be limited to on and off states, but may control intermediate power, such as a sleep mode state. In this sense, it may be more accurate to refer to the on/off controller 28 as a power state controller that can control multiple power states of the first patient monitor 10. The on state may also be referred to as a fully-on state.

The component values of R1, R2, and R3 and the voltage values V1, V2, V3, and Vout can vary depending on the application and automatic on/off circuit 26 implemented, but will generally be sized to achieve rated and proper operation of the automatic power on circuit components and the components of the first and second patient monitors 7, 10. In an example embodiment, R1 is 2,000 ohms, R2 is 10,000 ohms, R3 is 1,000 ohms, but again is not limited thereto. Additionally, V1 and V2 are approximately 1-5 volts DC and the voltage V3 may be a pulse voltage in the range of 0.5 mV to 2V DC.

The operation of the automatic on/off circuit 26 described above in FIG. 2A occurs when the second patient monitor 7 is positioned on, in, or proximate to the first patient monitor 10. The automatic power on circuit 26 establishes the coupling signal 22 between the portions of the automatic power on circuit 20, 21 in the respective patient monitors 7, 10. The coupling signal 22 activates the automatic power on circuit 26 and automatically controls the first patient monitor 10 to turn on when turned off or in a sleep mode without any user intervention.

That is, upon the activation of the automatic power on circuit 26, the first patient monitor 10 is controlled to turn on so as to match the on state of the second patient monitor 7. However, when the first patient monitor 10 is in an on/off state that already matches the on/off state of the second patient monitor 7 (i.e., prior to activation of the automatic power on circuit 26), the first patient monitor 10 will remain in a same on/off state after activation of the automatic power on circuit.

Figure 2B:
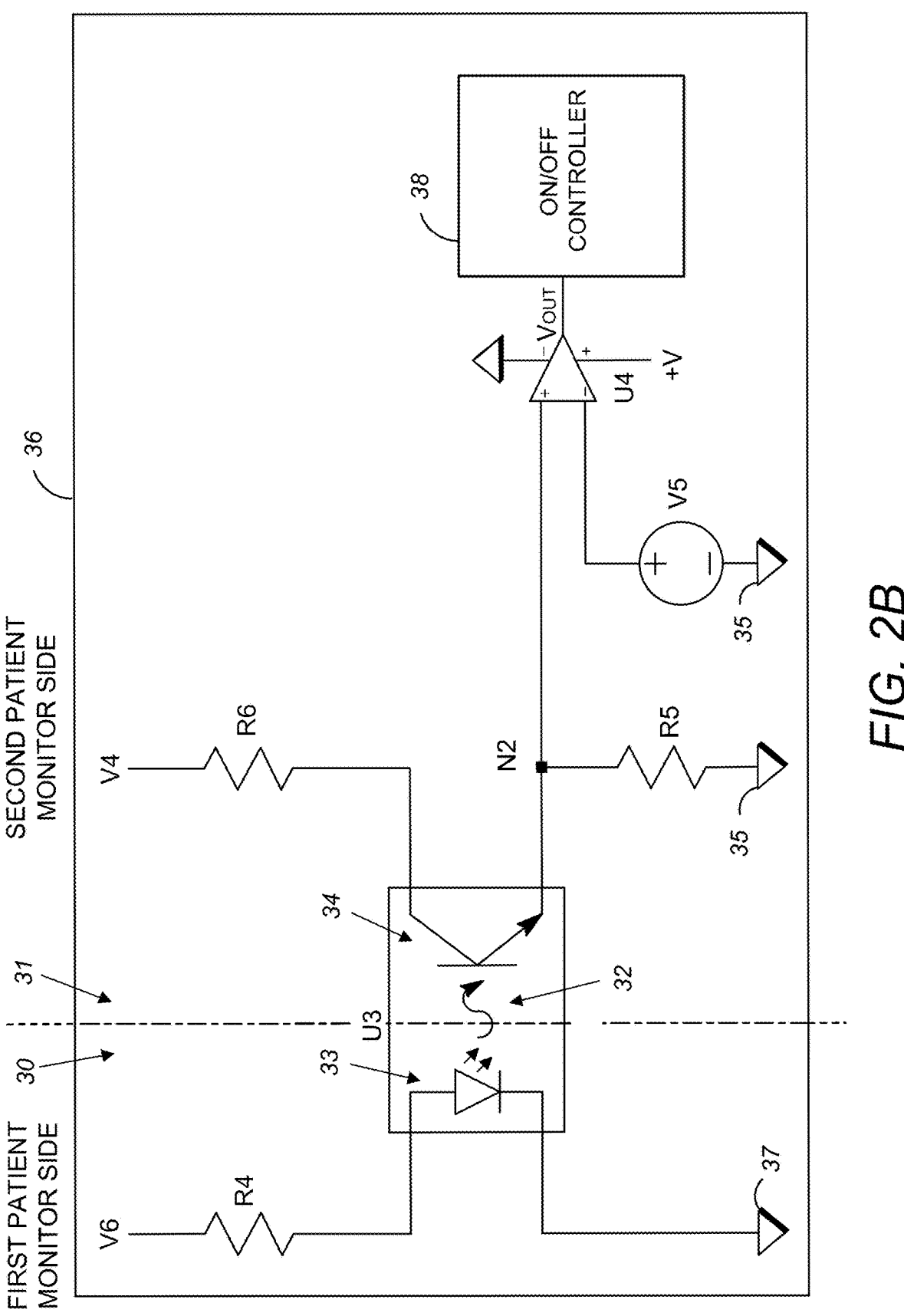
FIG. 2B is a schematic diagram of an automatic power on circuit according to one or more embodiments of the present disclosure.

FIG. 2B is a schematic diagram of an automatic power on circuit according to an embodiment of the present disclosure. The automatic power on circuit 36 in FIG. 2B is configured to operate in the reverse direction to the automatic power on circuit 26 of FIG. 2A. That is, an IR LED 33 is included in a portion of the automatic on/off circuit 30 on the first patient monitor side and a phototransistor 34 is included in a portion of the automatic on/off circuit 31 on the second patient monitor side.

The portion of the automatic on/off circuit 31 on the second patient monitor side is provided, for example, in the communications interface 9 of the second patient monitor 7 and receives power from the power source 6 through internal bus 5. The portion of the automatic on/off circuit 30 on the first patient monitor side is provided, for example, in the communications interface 14 of the first patient monitor 10 and receives power from the power source 16 through internal bus 11.

Similar to FIG. 2A, in FIG. 2B the automatic on/off circuit 36 includes a phototransistor circuit U3 that establishes a coupling connection 32 (e.g., coupling signal) between the portion of the automatic on/off circuit 30 and the portion of the automatic on/off circuit 31 using an infrared IR LED 33 and a phototransistor 34. However, it is also contemplated by the present disclosure that the automatic power on circuit 36 can be modified to establish a coupling signal 32 between the different portions 30, 31 of the automatic power on circuit 36 using radio frequency, near-field magnetic induction (NFMI), Bluetooth, WiFi, or other wireless means.

In FIG. 2B, it is assumed that the second patient monitor 7 has been positioned on, in, or proximate to the first patient monitor 10, such that a coupling signal 32 can be established between the portion of the automatic power on circuit 30 and the portion of the automatic power on circuit 31. Example configurations of the second patient monitor 7 positioned on, in, or proximate to the first patient monitor 10 for establishing the coupling signal 22 are discussed in more detail with reference to FIGS. 3, 5, 6A, and 6B.

In FIG. 2B, it is assumed that the power source 16 of the first patient monitor 10 is turned on and is providing power to the components of the first patient monitor 10, including the portion the automatic on/off circuit 30 on the first patient monitor side, as indicated by the voltage V6. The portion of automatic on/off circuit 30 is attached to ground 37 so that the applied voltage V6 causes a current to flow through resistor R4 and IR LED 33 of the phototransistor circuit U3. The current flowing through the IR LED 33 causes the IR LED to emit IR light as a coupling signal 32 toward the phototransistor 34 of the phototransistor circuit U3. The portion of the automatic on/off circuit 31 is attached to ground 35 so that the light received the phototransistor 34 activates the phototransistor 34 and causes current to flow through phototransistor 34 from the voltage V4 applied to the resistor R6. The voltage V4 is supplied from a connection to the power source 6 through the internal bus 5 of the second patient monitor 7.

The current flowing through the phototransistor 34 turns on an output of the comparator U4 and produce a voltage Vout from the automatic on/off circuit 31. Specifically, voltage Vout is generated by the comparator U4 when the voltage at node N2 exceeds the voltage of V5. Otherwise, the comparator U4 outputs 0V. The voltage Vout is provided to the switching circuitry of the on/off switch of the power source 6 of the second patient monitor 7 through the internal bus 5. The voltage Vout applied to the switching circuitry of the on/off switch of the power source 6 will automatically turn on the second patient monitor 7 when turned off or in a sleep mode.

In particular, the automatic on/off circuit 36 includes an on/off controller 38 that is connected to the output of the comparator U4 for receiving the control voltage Vout. The on/off controller 38 is configured to turn on and off power supplied from the power source 6 of the second patient monitor 7 based on the output of the comparator U4. For example, when the output of the comparator U4 is equal to Vout and the on/off controller 38 is in the off state or a sleep mode state, the on/off controller 38 is configured to turn on the power supply from the power source 6 such that components of the second patient monitor 7 receive power therefrom. When the output of the comparator U4 is equal to Vout and the on/off controller 38 is already in the on state, the on/off controller 38 is configured to maintain the on state from the power supply. In other words, when the on/off controller 38 is already in the on state, the output of the comparator U4 can be ignored.

As alluded to above, the on/off controller 38 may not be limited to on and off states, but may control intermediate power states, such as a sleep mode state. In this sense, it may be more accurate to refer to the on/off controller 38 as a power state controller that can control multiple power states of the second patient monitor 7. The on state may also be referred to as a fully-on state.

The component values of R4, R5, and R6 and the voltage values V4, V5, V6, and Vout can vary depending on the application and automatic on/off circuit 36 implemented, and will generally be sized to achieve rated and proper operation of the automatic power on circuit components and the components of the first and second patient monitors. In an example embodiment, R4 is 2,000 ohms, R5 is 10,000 ohms, R6 is 1,000 ohms, but again is not limited thereto. Additionally, V4 and V5 are approximately 3-5 volts DC and the voltage V3 may be a pulsed voltage in the range of 0.5 mV to 2V DC.

The operation of the automatic on/off circuit 36 described above in FIG. 2B occurs when the second patient monitor 7 is positioned on, in, or proximate to the first patient monitor 10. The automatic power on circuit 36 establishes the coupling signal 32 between the portion of the automatic power on circuit 30 on the first patient monitor side and the portion of the automatic power on circuit 31 on the second patient monitor side. The coupling signal 32 activates the automatic power on circuit 36 and automatically controls the second patient monitor 7 to turn on without user intervention.

That is, upon the activation of the automatic power on circuit 36, the second patient monitor 7 is controlled to turn on so as to match the on state of the first patient monitor 10. However, when the second patient monitor 7 is in an on/off state that already matches the on/off state of the first patient monitor 10 (i.e., prior to activation of the automatic power on circuit), the second patient monitor 7 will remain in the same on/off state after activation of the automatic power on circuit 36.

It is contemplated by the present disclosure that the automatic power on circuits 26, 36 described with reference to FIG. 2A and FIG. 2B can be implemented individually or together in the first and second patient monitors 7, 10. Additionally, it is contemplated by the present disclosure that there can be multiple automatic power on circuits 26, 36 implemented in the first and second patient monitors 7, 10 such that each of the first and second patient monitors 7, 10 can include multiple infrared IR LEDs and multiple phototransistors. The automatic power on circuits 26, 36 described with reference to FIG. 2A and FIG. 2B are implemented in the first and second patient monitors 7, 10 to accomplish the following operations without any user intervention:

1) If the second patient monitor 7 is powered ON and positioned on, in, or proximate to a powered OFF first patient monitor 10, the first patient monitor 10 will automatically be powered ON;

2) If the second patient monitor 7 is powered ON and positioned on, in, or proximate to a powered ON first patient monitor 10, the first patient monitor 10 and the second monitor 7 will remain ON;

3) If the second patient monitor 7 is powered OFF and positioned on, in, or proximate to a powered ON first patient monitor 10, the second patient monitor 7 will automatically be powered ON;

4) If the second patient monitor 7 is powered OFF and positioned on, in, or proximate to a powered OFF first patient monitor 10, the first patient monitor 10 and the second monitor 7 will remain OFF (e.g., because the coupling signal will not be generated);

5) If the second patient monitor 7 is powered ON, and is placed in a separate monitor mount (e.g., not positioned on, in, or proximate to the first patient monitor 10, the second patient monitor 7 will remain ON;

6) If the second patient monitor 7 is powered OFF, and is placed in a separate monitor mount (e.g., not positioned on, in, or proximate to the first patient), the second patient monitor 7 will remain OFF (e.g., because the coupling signal will not be generated);

7) If the first patient monitor 10 is powered ON, and is placed in a separate monitor mount (e.g., not positioned on, in, or proximate to the second patient monitor), the first patient monitor 10 will remain ON; and 8) If the first patient monitor 10 is powered OFF, and is placed in a separate monitor mount (e.g., not positioned on, in, or proximate to the second patient), the first patient monitor 10 will remain OFF (e.g., because the coupling signal will not be generated).

In certain embodiments, the first patient monitor 10 or the second patient monitor 7 may employ a safety feature wherein the power OFF button needs to be depressed for a certain interval of time, such as without limitation five seconds or greater, to power OFF the device to avoid an inadvertent powering down of either or both monitors.

The automatic power on circuits 26, 36 described with reference to FIG. 2A and FIG. 2B provide improvements and advantages over prior art systems.

For example, when a patient is being transported between different patient care or hospital environments, clinicians are required to perform manual operations when transitioning between different medical devices (e.g., attaching cables or pushing of buttons on the front panel of a smaller transportable medical device or a larger stationary or portable medical device). This manual action increases workload on clinicians and increases the overall time for performing accurate patient assessment during transport of the patient between different patient care or hospital environments.

The automatic power on circuits 26, 36, described with reference to FIG. 2A and FIG. 2B, allow for seamless and automatic control of the power states of medical devices in a way that reduces work load on clinicians and supports rapid patient assessment during the transport of patients between different patient care or hospital environments, which can be particularly advantageous when used in critical care environments where rapid assessment of a patient's condition is imperative.

Additional advantages of the automatic power on circuit 26, 36 described with reference to FIG. 2A and FIG. 2B of the present disclosure include overcoming the limitations of the smaller portable medical device in displaying information (e.g., physiological parameters) on a small-sized display. That is, the large-sized display of a larger stationary or portable medical device can be used to display information (e.g., patient data, medical history from EMR or other similar information) in various configurations that are easier for clinical providers to review without users' intervention to manually turn on/off the device. Furthermore, the larger medical device may be in communication with other medical devices (e.g., insulin pumps, or ventilators) such that more information can be displayed to clinical providers to review. The automatic power on circuit in accordance with the present disclosure may advantageously facilitate the continuous monitoring and information display on patient monitors wherever the patient being monitored is located (e.g., patient ward, ambulance, or operation room).

Figure 3:
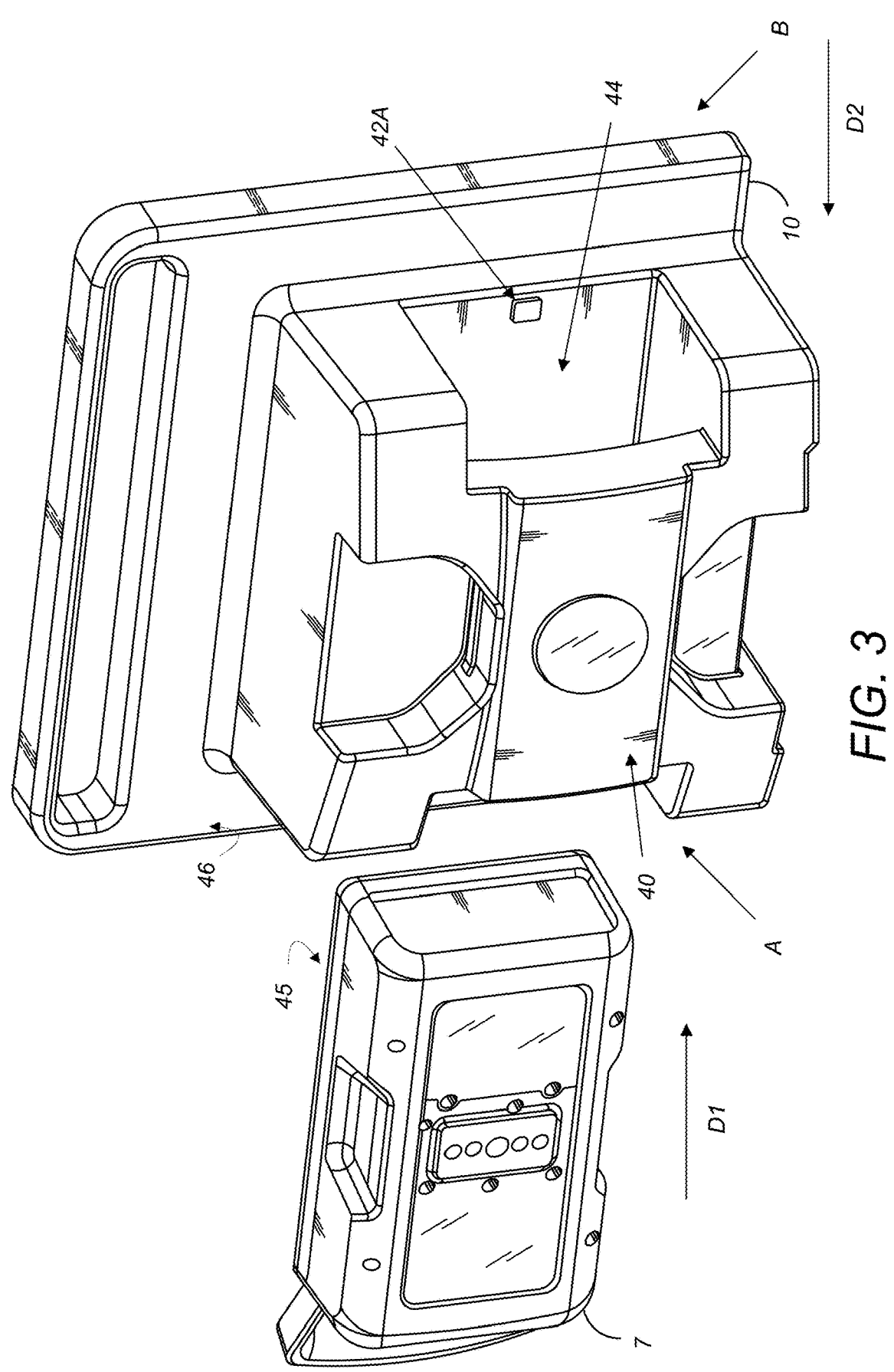
FIG. 3 illustrates an example configuration of the positioning of a first patient monitor and a second patient monitor according to one or more embodiments of the present disclosure.

FIG. 3 illustrates an example configuration of the second patient monitor 7 just prior to being positioned on, in, or proximate to the first patient monitor 10. As shown in FIG. 3, the second patient monitor 7 has a size and/or shape so as to be received within the cavity 44 of the mounting area 40 located on the back surface 46 of the first patient monitor 10, when moved in direction D1 on side A of the first patient monitor 10. The second patient monitor 7 can also be received within the cavity 44 of the mounting area 40 of the first patient monitor 10 when moved in direction D2 on side B of the first patient monitor 10, by simply rotating the second patient monitor 7 by 180 degrees prior to being inserted into the cavity 44. Thus, the housing of the second patient monitor 7 slides into the cavity 44 that is configured to receive the second patient monitor 7.

The coupling signal 22, 32 between the different portions of the automatic on/off circuit 20, 21, 30, 31 in the first and second patient monitors 7, 10, which establishes the communication connection 18 (e.g., as described in FIGS. 2A and 2B), is made possible by providing one or more openings or windows 42A in the covers or shells of the first and second patient monitors 7, 10.

In this embodiment, an example opening or window 42A can be seen on the back surface 46 of the cover or shell (i.e., housing) on the right-side of the first patient monitor 10 arranged within the mounting area 40 (e.g., to accommodate when the second patient monitor 7 is moved in direction D1 on side A of the first patient monitor 10). However, it is contemplated by the present disclosure that an opening or window 42B (e.g., FIG. 4B) can be provided on the back surface 46 of the cover or shell on the left-side of the first patient monitor 10 (e.g., to accommodate when the second patient monitor 7 is moved in direction D2 on side B of the first patient monitor 10).

As shown in FIG. 3, the opening or window 42A is a certain size and/or shape on the back surface 46 of the first patient monitor 10. However, it is contemplated by the present disclosure that the openings or windows 42A, 42B can be virtually any size and/or shape and located on other surfaces of the first patient monitor 10. Additionally, there can also be one or more of the openings or windows 42A, 42B (e.g., FIG. 4B) in the cover or shell on the of the first patient monitor 10 for establishing coupling signals 22, 32 between the different portions of the automatic on/off circuit 20, 21, 30, 31 in the first and second patient monitors 7, 10. Regardless of the location, size and/or shape, and number of openings or windows 42A, 42B provided in the cover or shell of the first patient monitor 10, the second patient monitor 7 will have one or more openings or windows 65A, 65B (e.g., FIG. 4A) in its cover or shell (i.e., housing), for example, on its front surface 45, which would correspond to the one or more openings or windows 42A, 42B on the cover or shell of the first patient monitor 10. The IR transmitting and receiving circuitry are arranged inside their respective housings behind a window or opening.

Thus, when the second patient monitor 7 is inserted into the cavity 44 of the mounting area 40 (e.g., by moving in direction D1 on side A or moving in direction D2 on side B), the one or more openings or windows 65A, 65B of the second patient monitor 7 would align with the one or more corresponding openings or windows 42A, 42B of the first patient monitor 10 such that light from the IR LED 23, 33 in one portion of the automatic power on circuit 20, 30 passes through the openings or windows 42A, 42B, 65A, 65B and is received by the phototransistor 24, 34 located in the other portion of the automatic power on or circuit 21, 31.

Figure 4A:
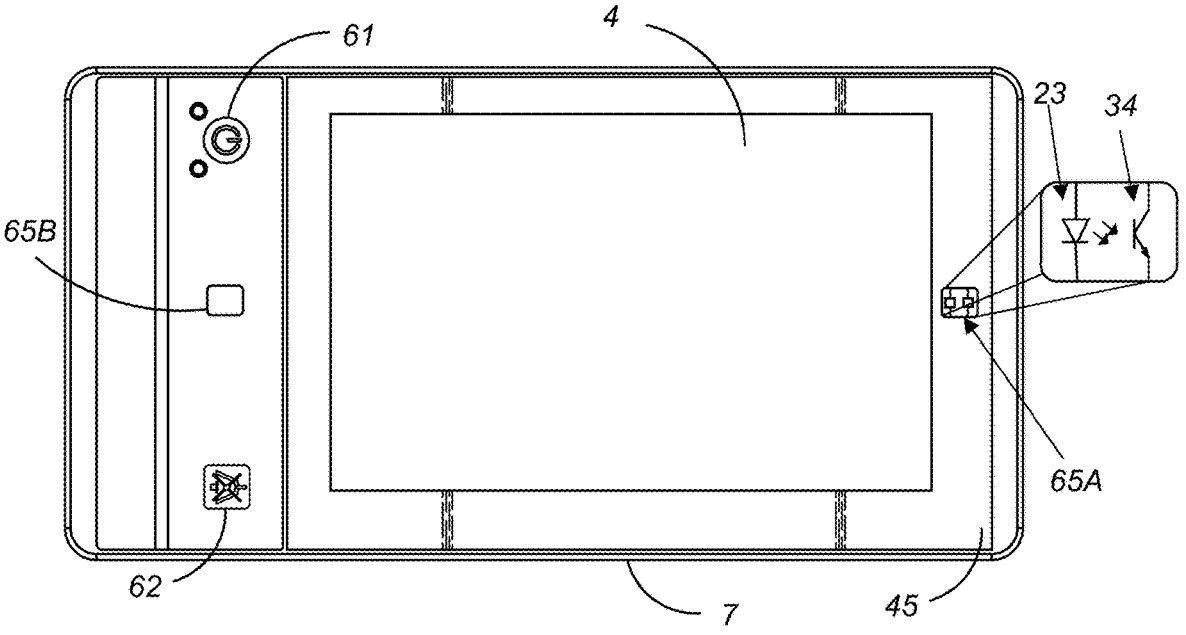
FIG. 4A illustrates a front view of the second patient monitor according to one or more embodiments of the present disclosure.
Figure 4B:
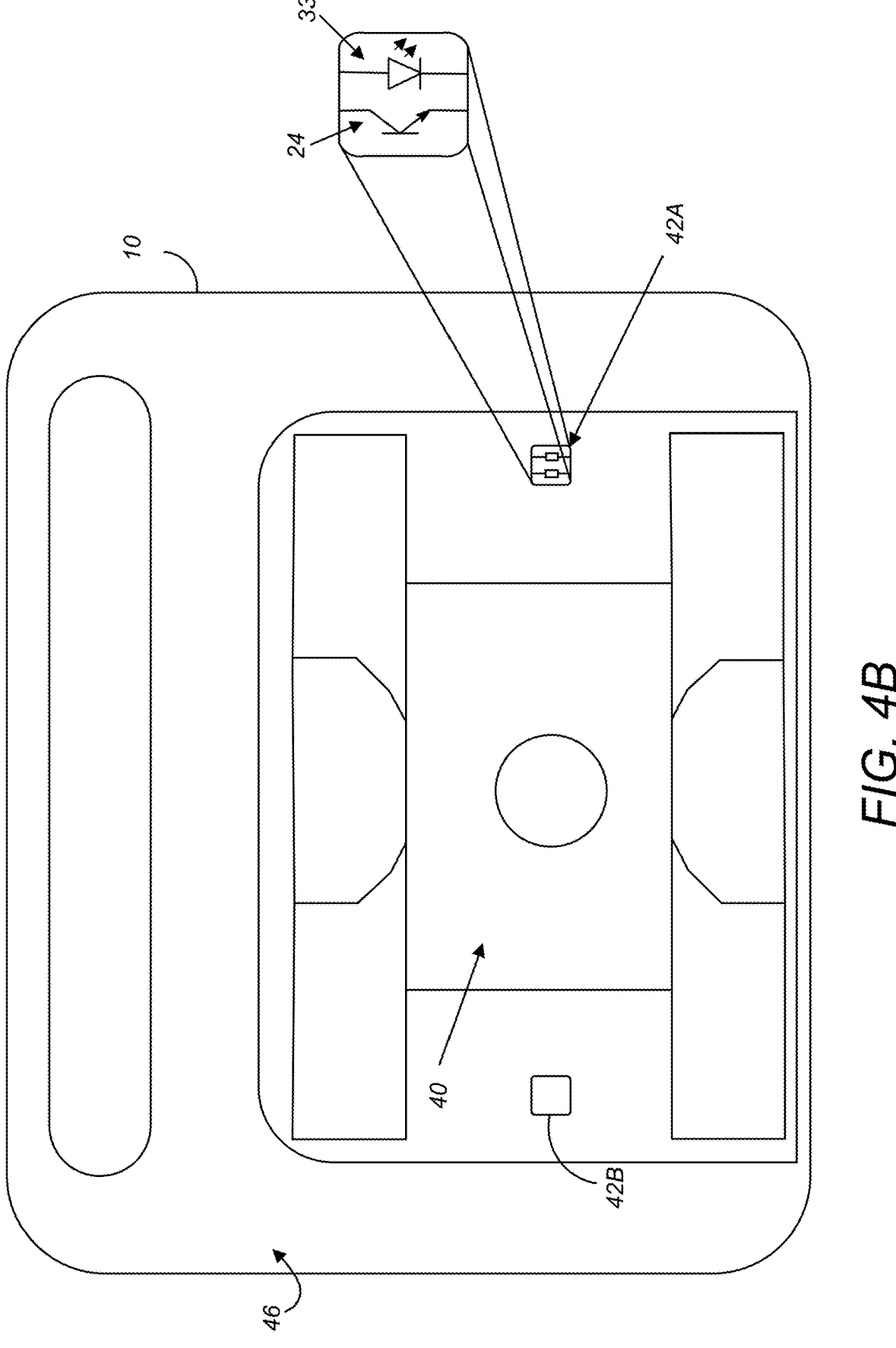
FIG. 4B illustrates a back view of the first patient monitor according to one or more embodiments of the present disclosure.

FIG. 4A illustrates an example front view of the second patient monitor 7 and FIG. 4B illustrates an example back view of the first patient monitor 10.

As shown in FIG. 4A, the front surface 45 of the second patient monitor 7 includes the display/GUI 4, a manual power switch 61, openings or windows 65A, 65B in the shell or cover (i.e., housing), and an icon 62 indicating, for example, a charging state of the second patient monitor 7. The openings or windows 65A, 65B are provided in the cover or shell of the second patient monitor 7 and allow light to pass through the shell or cover to and from the portions of the automatic power on circuit 20, 31 in the second patient monitor 7. For example, as shown in the expanded view of the opening or window 65A of the second patient monitor 7, the coupling signal 22 transmitted from the IR LED 23 in the portion of the automatic on/off circuit 20 will be allowed to pass through the window 65A of the second patient monitor 7 to be received by the phototransistor 24 in the portion of the automatic on/off circuit 21 of the first patient monitor 10. Additionally, the coupling signal 32 transmitted from the IR LED 33 in the portion of the automatic on/off circuit 30 would be allowed to pass through the window 65A and be received by the phototransistor 34 in the portion of the automatic on/off circuit 31 in the second patient monitor 7.

As shown in FIG. 4A, there are two openings or windows 65A, 65B of a certain size and/or shape located on the front surface 45 of the second patient monitor 7. However, it is contemplated by the present disclosure that the openings or windows 65A, 65B can be any size and/or shape and located on other surfaces of the second patient monitor 7. Additionally, there can be one or several openings or windows 65A, 65B in the cover or shell on the of the second patient monitor 7 for establishing the coupling signal 22, 32 between the different portions of the automatic on/off circuit 20, 21, 30, 31 in the first and second patient monitors 7, 10. Regardless of the location, size and/or shape, and number of openings or windows 65A, 65B provided on the cover or shell of the second patient monitor 7, the first patient monitor 10 will have one or more openings or windows 42A, 42B (e.g., FIG. 4B) on its cover or shell, for example, on a back surface 46, which would correspond to the one or more openings or windows 65A, 65B in the cover or shell of the second patient monitor 7.

FIG. 4B shows the back view of the first patient monitor 10. As shown in FIG. 4B, the back surface 46 of the first patient monitor 10 includes openings or windows 42A, 42B in the shell or cover within the mounting area 40 of the first patient monitor 10. The openings or windows 42A, 42B are provided in the cover or shell of the first patient monitor 10 to allow light to pass through the shell or cover to and from the portions of the automatic power on circuit 21, 30 in the first patient monitor 10.

For example, as shown in the expanded view of the opening or window 42A of the first patient monitor 10, the coupling signal 32 transmitted from the IR LED 33 in the portion of the automatic on/off circuit 30 will be allowed to pass through the window 42A of the first patient monitor 10 to be received by the phototransistor 34 in the portion of the automatic on/off circuit 31 of the second patient monitor 7. Additionally, the coupling signal 22 transmitted from the IR LED 23 in the portion of the automatic on/off circuit 20 would be allowed to pass through the window 42A and be received by the phototransistor 24 in the portion of the automatic on/off circuit 21 in the first patient monitor 10.

Thus, when the second patient monitor 7 is inserted into the cavity 44 of the mounting area 40 (e.g., by moving in direction D1 on side A or moving in direction D2 on side B), the one or more openings or windows 65A, 65B of the second patient monitor 7 align with the one or more corresponding openings or windows 42A, 42B of the first patient monitor 10 such that light from the IR LED 23, 33 in one portion of the automatic power on circuit 20, 30 passes through the openings or windows 42A, 42B, 65A, 65B and is received by the phototransistor 24, 34 located in the other portion of the automatic power on or circuit 21, 31. Once the coupling signal 22, 32 is established in the automatic power on circuit 26, 36, the automatic power on circuit 26, 36 will be activated and operate as described with reference to FIGS. 2A and 2B.

FIGS. 3, 4A, and 4B show example locations of openings or windows 42A, 42B, 65A, 65B in the shells or covers of the first and second patient monitors 7, 10 for achieving alignment and coupling of the different portions of the automatic on/off circuit 20, 21, 30, 31. However, it is contemplated by the present disclosure that there could be one or more openings or windows 42A, 42B, 65A, 65B located on any surface of the first and second patient monitors 7, 10 as long as the location of the one or more openings or windows 42A, 42B, 65A, 65B are capable of achieving alignment and coupling of the different portions of the automatic on/off circuit 20, 21, 30, 31. Additionally, the openings or windows 42A, 42B, 65A, 65B may be covered by a material which allows light to be pass through, and the material may be visually transparent or opaque.

It is also contemplated by an embodiment of the present disclosure that the openings or windows 42A, 42B, 65A, 65B in the shells or covers of the first and second patient monitors 7, 10 may not be necessary for achieving coupling of the different portions of the automatic on/off circuit. For example, the automatic power on circuit may be modified to establish a coupling signal between the different portions of the automatic power on circuit by using radio frequency, near-field magnetic induction (NFMI), Bluetooth, or WiFi. In these embodiments, it would only be necessary to position the second patient monitor 7 in, on, or proximate to the first patient monitor 10 to achieve coupling of the different portions of the automatic on/off circuit and activation of the automatic power on circuit. That is, no opening or window in the shells or covers of the first and second patient monitors 7, 10 would be necessary.

Figure 5:
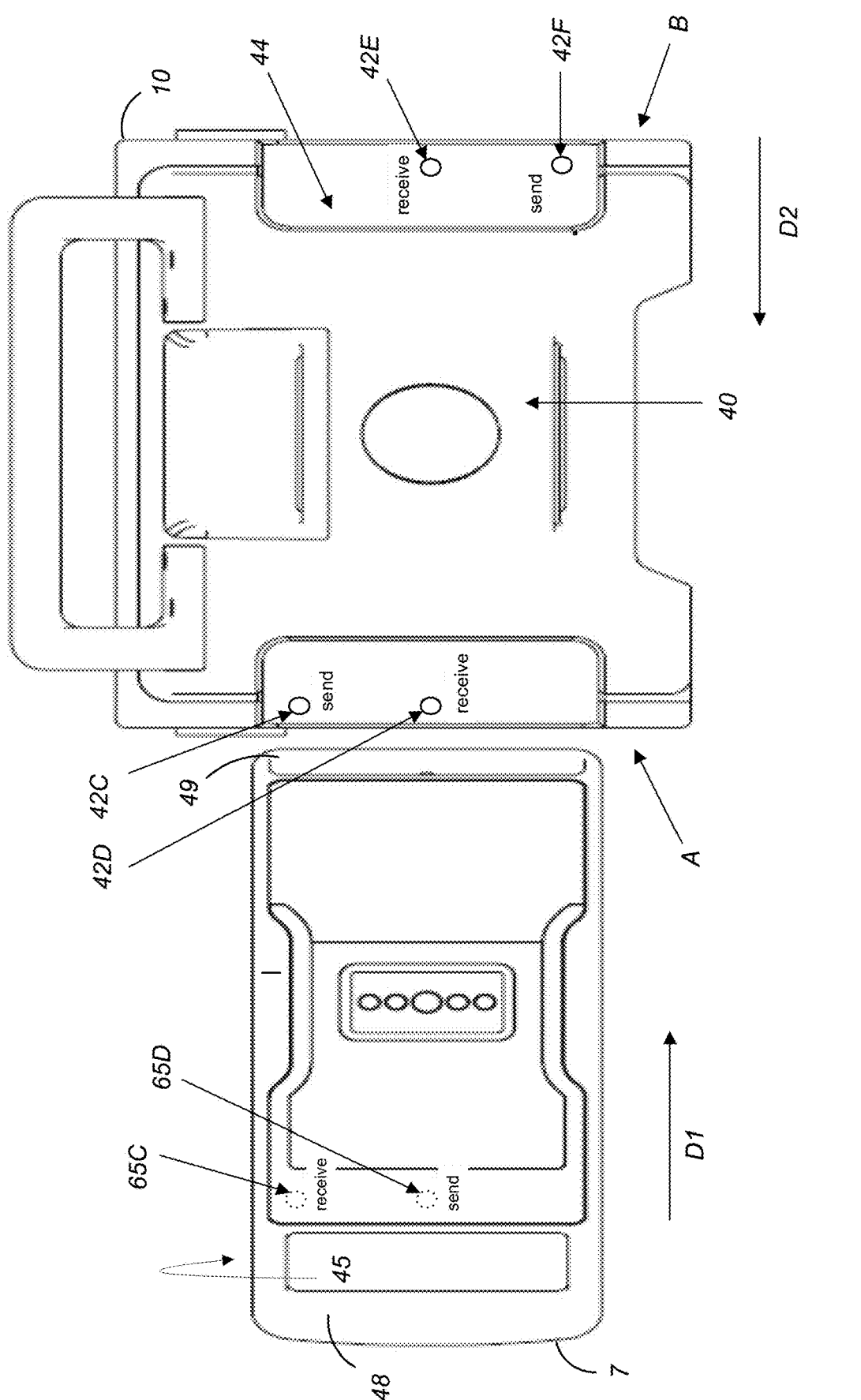
FIG. 5 illustrates an example configuration of the positioning of a first patient monitor and a second patient monitor according to one or more embodiments of the present disclosure.

FIG. 5 illustrates an example configuration of the positioning of a first patient monitor and a second patient monitor according to another embodiment of the present disclosure.

Similar to FIG. 3, in FIG. 5 the second patient monitor 7 has a size and/or shape so as to be received within the cavity 44 of the mounting area 40 of the first patient monitor 10, when moved in direction D1 on side A of the first patient monitor 10. The second patient monitor 7 can also be received within the cavity 44 of the mounting area 40 of the first patient monitor 10 when moved in direction D2 on side B of the first patient monitor 10, by simply rotating the second patient monitor 7 by 180 degrees prior to being inserted into the cavity 44.

The coupling signal 22, 32 between the different portions of the automatic on/off circuit 20, 21, 30, 31 in the first and second patient monitors 7, 10, which establishes the communication connection 18 (e.g., as described in FIGS. 2A and 2B), is made possible by the openings or windows 65C, 65D in the cover or shell second patient monitor 7 and the openings or windows 42C, 42D, 42E, 42F in the cover or shell of the first patient monitor 10.

The second patient monitor 7 includes two opening or windows 65C, 65D on the front surface 45 of the second patient monitor 7. In FIG. 5, the opening or windows 65C, 65D of the second patient monitor 7 are represented using dotted lines on the back of the second patient monitor 7 as an indication of the positioning of the openings or windows 65C, 65D on the front surface 45. The openings or windows 65C, 65D allow light to pass through the shell or cover to and from the portions of the automatic power on circuit 20, 31 in the second patient monitor 7. For example, the coupling signal 22 transmitted from the IR LED 23 in the portion of the automatic on/off circuit 20 will be allowed to pass through the window 65D of the second patient monitor 7 to be received by the phototransistor 24 in the portion of the automatic on/off circuit 21 of the first patient monitor 10. Additionally, the coupling signal 32 transmitted from the IR LED 33 in the portion of the automatic on/off circuit 30 would be allowed to pass through the window 65C and be received by the phototransistor 34 in the portion of the automatic on/off circuit 31 in the second patient monitor 7. That is, the IR LED 23 in one portion of the automatic power on circuit 20 may be positioned within one opening or window 65D (labeled as "send") in the shell or cover of the second monitor 7, while the phototransistor 34 in the other portion of the automatic power on circuit 31 may be positioned within another or a different opening or window 65C (labeled as "receive") in the shell or cover of the second monitor 7.

Likewise, as shown in FIG. 5, the first monitor 10 may include several openings or windows 42C, 42D, 42E, 42F, where the IR LED 33 and the phototransistor 24 can be respectively positioned. The openings or windows 42C, 42D, 42E, 42F are provided in the cover or shell of the first patient monitor 10 to allow light to pass through the shell or cover to and from the portions of the automatic power on circuit 21, 30 in the first patient monitor 10.

For example, when the second monitor 7 is inserted into the cavity 44 of the first patient monitor 10 in the direction D1, the coupling signal 32 transmitted from the IR LED 33 in the portion of the automatic on/off circuit 30 will be allowed to pass through the window 42C of the first patient monitor 10 to be received by the phototransistor 34 in the portion of the automatic on/off circuit 31 of the second patient monitor 7. Additionally, the coupling signal 22 transmitted from the IR LED 23 in the portion of the automatic on/off circuit 20 would be allowed to pass through the window 42D and be received by the phototransistor 24 in the portion of the automatic on/off circuit 21 in the first patient monitor 10.

That is, the IR LED 33 in one portion of the automatic power on circuit 30 may be positioned within one opening or window 42C (labeled as "send") in the shell or cover of the first monitor 10, while the phototransistor 24 included in the phototransistor in the other portion of the automatic power on circuit 21 may be positioned within another or a different opening or window 42D (labeled as "receive") in the shell or cover of the first monitor 10.

As another example, when the second monitor 7 is inserted into the cavity 44 of the first patient monitor 10 in the direction D2 (e.g., by simply rotating or inverting the second patient monitor 7 by 180 degrees prior to the insertion), the coupling signal 32 transmitted from the IR LED 33 in the portion of the automatic on/off circuit 30 will be allowed to pass through the window 42F of the first patient monitor 10 to be received by the phototransistor 34 in the portion of the automatic on/off circuit 31 of the second patient monitor 7. Additionally, the coupling signal 22 transmitted from the IR LED 23 in the portion of the automatic on/off circuit 20 would be allowed to pass through the window 42E and be received by the phototransistor 24 in the portion of the automatic on/off circuit 21 in the first patient monitor 10.

Here, the windows 42E and 42F are inverted with respect to windows 42C and 42D so that they align with windows 65C and 65D based on the orientation of the second patient monitor 7 when inserted into the mounting area 40. The second patient monitor 7 may include a handle 48 at one side that facilitates the insertion of the second patient monitor 7 into the mounting area 40 and the extraction therefrom. The non-handle side 49 of the second patient monitor 7 is inserted first into the mounting area 40 regardless of the insertion direction D1 or D2. The front side of the second patient monitor 7 faces towards the back side of the first patient monitor 10 regardless of insertion direction D1 or D2. Thus, the second patient monitor 7 is inverted when being inserted from direction D2 relative to when being inserted from direction D1.

That is, the IR LED 33 in one portion of the automatic power on circuit 30 may be positioned within one opening or window 42F (labeled as "send") in the shell or cover of the first monitor 10, while the phototransistor 24 included in the other portion of the automatic power on circuit 21 may be positioned within another or a different opening or window 42E (labeled as "receive") in the shell or cover of the first monitor 10.

Therefore, when the second monitor 7 is inserted into the cavity 44 of the first patient monitor 10 in the direction D1 or in the direction D2 (e.g., simply by rotating or inverting the second monitor 7 by 180 degree prior to the insertion), the openings or windows 42C, 42D, 42E, 42F, 65C, 65D on the corresponding surfaces of the first and second patient monitors 7, 10 align such that light from the IR LED 23, 33 in one portion of the automatic power on circuit 20, 30 passes through the openings or windows 42C, 42D, 42E, 42F, 65C, 65D and is received by the phototransistor 24, 34 located in the other portion of the automatic power on or circuit 21, 31.

FIG. 5 shows example locations of openings or windows 42C, 42D, 42E, 42F, 65C, 65D in the shells or covers of the first and second patient monitors 7, 10 for achieving alignment and coupling of the different portions of the automatic on/off circuit 20, 21, 30, 31. However, it is contemplated by the present disclosure that there could be one or more openings or windows 42C, 42D, 42E, 42F, 65C, 65D located on any surface or portion of the first and second patient monitors 7, 10 as long as the location of the one or more openings or windows 42C, 42D, 42E, 42F, 65C, 65D are capable of achieving alignment and coupling of the different portions of the automatic on/off circuit 20, 21, 30, 31. Additionally, the openings or windows 42C, 42D, 42E, 42F,

65C, 65D may be covered by a material which allows light to be pass through, and the material may be visually transparent or opaque.

It is also contemplated by an embodiment of the present disclosure that the openings or windows 42C, 42D, 42E, 42F, 65C, 65D in the shells or covers of the first and second patient monitors 7, 10 may not be necessary for achieving the coupling of the different portions of the automatic on/off circuit. For example, the automatic power on circuit may be modified to establish a coupling signal between the different portions of the automatic power on circuit by using radio frequency, near-field magnetic induction (NFMI), Bluetooth, or WiFi. In these embodiments, it would only be necessary to position the second patient monitor 7 in, on, or proximate to the first patient monitor 10 to achieve coupling of the different portions of the automatic on/off circuit and activation of the automatic power on circuit. That is, no opening or window in the shells or covers of the first and second patient monitors 7, 10 would be necessary.

Figure 6A:
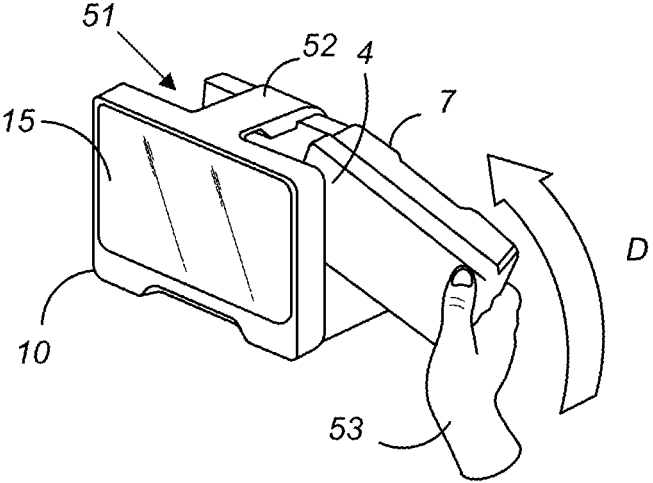
FIGS. 6A and 6B illustrate an example configuration of the positioning of a first patient monitor and a second patient monitor according to one or more embodiments of the present disclosure.
Figure 6B:
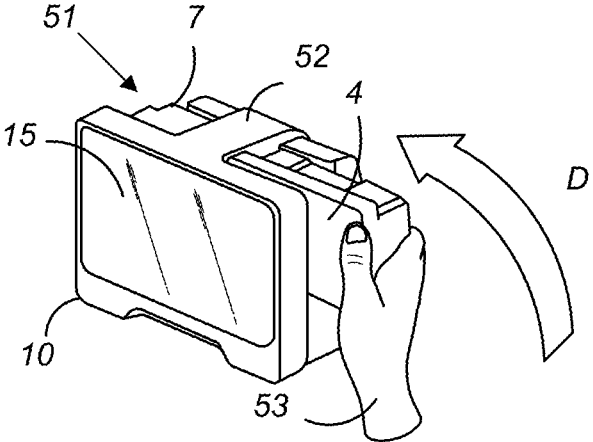

FIGS. 6A and 6B illustrate another example configuration of the positioning of a first monitor and a second monitor according to an embodiment of the present disclosure.

FIGS. 6A and 6B are front views of the first patient monitor 10 and second patient monitor 7 such that the respective displays/GUIs 4, 15 are visible. As shown in FIGS. 6A and 6B, the second patient monitor 7 is being inserted into the opening or cavity 51 that defines a mounting area of the first patient monitor 10. The user 53 inserts the second patient monitor 7 by first holding the second patient monitor 7 with one hand and then inserting the second patient monitor 7 into the cavity 51 of the first patient monitor 10 while rotating it upwardly in a direction D until fully inserted into the opening or cavity 51. Such insertion and removal of the second patient monitor 7 with respect to the first patient monitor 10 can be performed with one hand by the user 53 to achieve coupling of the different portions of the automatic on/off circuit 20, 21, 30, 31 and activation of the automatic power on circuit 26, 36. In other words, it is not necessary to perform two separate motions to insert or remove the second patient monitor 7 from the first patient monitor 10.

In an embodiment of the present disclosure, area structural bridge 52 may provide structural support between front and rear sides of the first patient monitor 10, as well as assist in mechanically securing the second patient monitor 7 within the opening 51 (i.e., the mounting area).

Alternatively, the first patient monitor 10 may have an open top portion instead of open side portions such that the second patient monitor 7 can be inserted into the first patient monitor 10 from above to achieve coupling of the different portions of the automatic on/off circuit 20, 21, 30, 31 and activation of the automatic power on circuit 26, 36.

Additionally, in an embodiment of the present disclosure, the mounting area may be completely open on the top, sides, and back such that the second patient monitor 7 is placed on a bottom surface (e.g., single surface) of the mounting area to achieve coupling of the different portions of the automatic on/off circuit 20, 21, 30, 31 and activation of the automatic power on circuit 26, 36.

Although not shown in FIGS. 6A and 6B, it is contemplated by this embodiment of the present disclosure that one or more openings or windows 42A, 42B, 42C, 42D, 42E, 42F, 65A, 65B, 65C, 65D may be used in the shells or covers (i.e., housings) of the first and second patient monitors 7, 10 to achieve alignment and coupling of the different portions of the automatic on/off circuit 20, 21, 30, 31. The openings or windows 42A, 42B, 42C, 42D, 42E, 42F, 65A, 65B, 65C, 65D may be located on any surface or portion of the first and second patient monitors 7, 10, which is capable of achieving alignment and coupling of the different portions of the automatic on/off circuit 20, 21, 30, 31 when the second patient monitor 7 is position in, on, or proximate to the first patient monitor 10.

It is also contemplated by an embodiment of the present disclosure that the automatic power on circuit 26, 36 could be modified to establish a coupling signal between the different portions of the automatic power on circuit using radio frequency, near-field magnetic induction (NFMI), Bluetooth, or WiFi. Accordingly, it would only be necessary to position the second patient monitor 7 in, on, or proximate to the first patient monitor 10 to achieve coupling of the different portions of the automatic on/off circuit and activation of the automatic power on circuit 26, 36. No opening or window in the shells or covers of the first and second patient monitors 7, 10 would be necessary.

Figure 7:
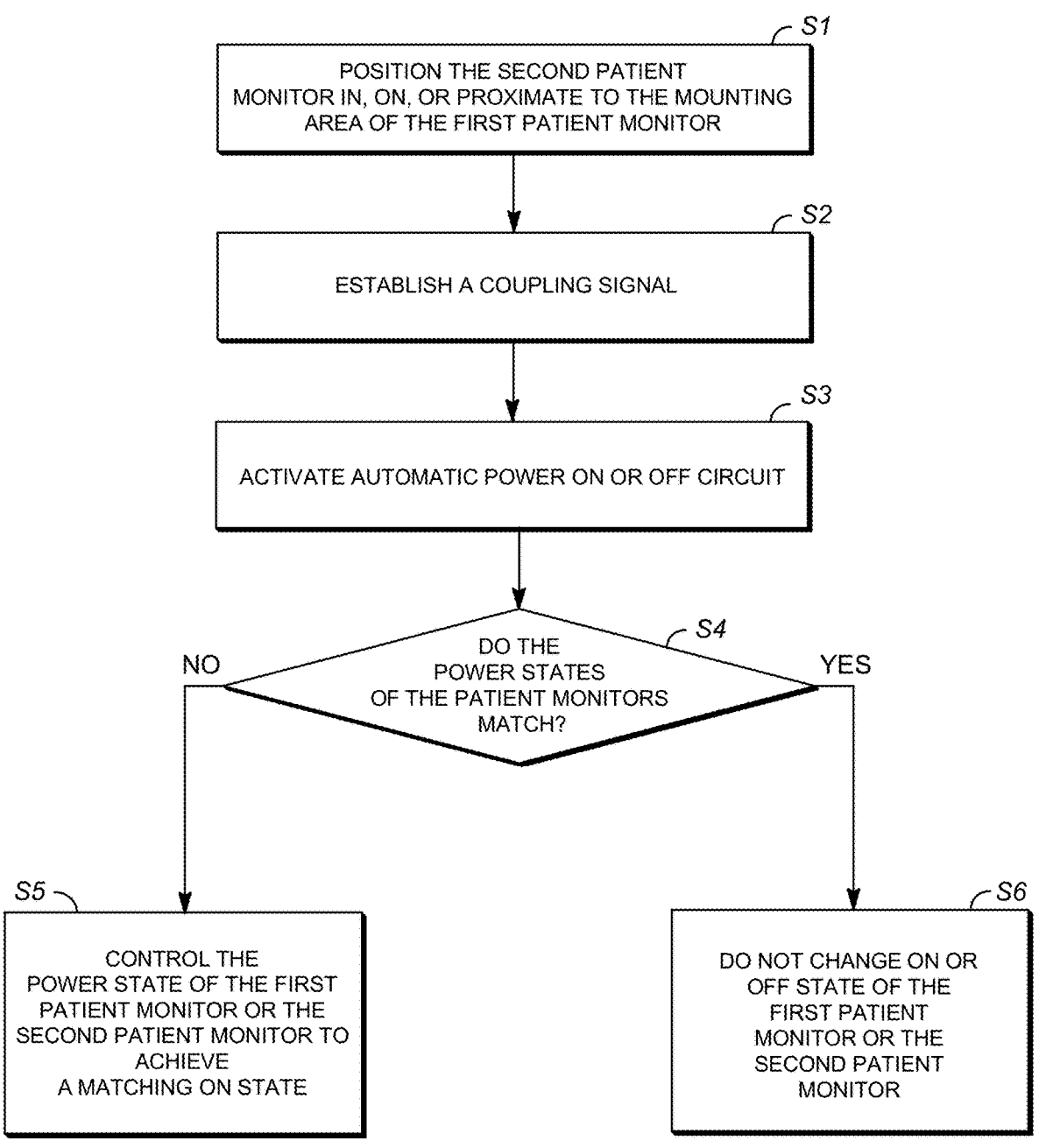
FIG. 7 illustrates an automatic power on method according to one or more embodiments of the present disclosure.

FIG. 7 illustrates an example patient monitor automatic power on method according to an embodiment of the present disclosure.

In Step S1, the second patient monitor 7 is positioned on, in, or proximate to the mounting area of the first patient monitor 10. For example, as described with reference to FIGS. 3 and 5, the second patient monitor 7 has a size and/or shape so as to be received within a cavity 44 of a mounting area 40 located on the back surface 46 of the first patient monitor 10 when moved in direction D1 or D2.

As described with reference to FIGS. 6A and 6B, the user 53 inserts the second patient monitor 7 by first holding the second patient monitor 7 with one hand and then inserting the second patient monitor 7 into the cavity 51 of the first patient monitor 10 while rotating it upwardly in direction D until fully inserted into the opening or cavity 51. Additionally, the mounting area may have an open top portion instead of open side portions such that the second patient monitor 7 can be inserted into the first patient monitor 10 from above.

In another embodiment of the present disclosure, the mounting area may be completely open on the top, sides, and back such that the second patient monitor is place on a bottom surface (i.e., a single surface) of the mounting area.

Once the second patient monitor 7 is positioned on, in, or proximate to the mounting area of the first patient monitor 10 in Step 2, a coupling signal 22, 32 is established between the different portions of automatic on/off circuits 20, 21, 30, 31 in the first and second patient monitors 7, 10.

For example, as described with reference to FIGS. 2A, 2B, 3, 4A, 4B, and 5 the coupling signals 22, 32 between the different portions of automatic on/off circuit 20, 21, 30, 31 in the first and second patient monitors 7, 10 establishes the communication connection 18 by providing one or more openings or windows 42A, 42B, 42C, 42D, 42E, 42F, 65A, 65B, 65C, 65D in the covers or shells of the first and second patient monitors 7, 10.

When the second patient monitor 7 is inserted into the cavity 44 of the mounting area 40 (i.e., by moving in direction D1 or D2), the openings or windows 42A, 42B, 42C, 42D, 42E, 42F, 65A, 65B, 65C, 65D on the corresponding surfaces of the first and second patient monitors 7, 10 align such that the light from the IR LED 23, 33 in one portion of the automatic power on circuit 20, 30 would pass through the openings or windows 42A, 42B, 42C, 42D, 42E, 42F, 65A, 65B, 65C, 65D and be received by the phototransistor 24, 34 located in the other portion of the automatic power on or circuit 21, 31.

FIGS. 3, 4A, 4B, and 5 show example locations of the openings or windows 42A, 42B, 42C, 42D, 42E, 42F, 65A,

65B, 65C, 65D in the shells or covers of the first and second patient monitors 7, 10 for achieving alignment and coupling of the different portions of the automatic on/off circuit 20, 21, 30, 31. However, it is contemplated by the present disclosure that one or more openings or windows 42A, 42B, 42C, 42D, 42E, 42F, 65A, 65B, 65C, 65D may be located on any surface or portion of the first and second patient monitors 7, 10 as long as the location of the one or more openings or windows 42A, 42B, 42C, 42D, 42E, 42F, 65A, 65B, 65C, 65D are capable of achieving alignment and coupling of the different portions of the automatic on/off circuit 20, 21, 30, 31.

It is also contemplated by an embodiment of the present disclosure that the automatic power on circuit may be modified to establish a coupling signal between the different portions of the automatic power on circuit by using radio frequency, near-field magnetic induction (NFMI), Bluetooth, or WiFi. In this embodiment, it would only be necessary to position the second patient monitor 7 in, on, or proximate to the first patient monitor 10 to achieve coupling of the different portions of the automatic on/off circuit and activation of the automatic power on circuit. No opening or window in the shells or covers of the first and second patient monitors 7, 10 would be necessary.

Once a coupling signal 22, 32 is established between the different portions of automatic on/off circuits 20, 21, 30, 31 in the first and second patient monitors 7, 10 in Step S2, in Step S3 the automatic power on circuit 26, 36 is activated, as previously described in detail with reference to FIGS. 2A and 2B.

As described with reference to FIG. 2A, the power supply from the power source 6 of the second patient monitor 7 is turned on and is providing power to the components of the second patient monitor 7. The power supply from the power source 6 may be "turned on" by establishing one or more connections from the power source 6 to a power bus that is connected to components of the second patient monitor 7 by, for example, closing one or more switches that routes power to the power bus. The power bus distributes the power from the power source 6, thereby fully turning on the second patient monitor 7. The coupling signal 22 activates the automatic power on circuit 26 and automatically controls the power state of first patient monitor 10 without user intervention.

For example, upon the activation of the automatic power on circuit 26 in Step S3, if the first patient monitor 10 is off or in a sleep mode, the first patient monitor 10 is controlled by the automatic power on circuit 26 to automatically turn on so as to match the on state of the second patient monitor 7, as indicated in Steps S4 and S5. However, if first patient monitor 10 is in an on state that already matches the on state of the second patient monitor 7, the first patient monitor 10 will remain in the same power on state after activation of the automatic power on circuit, as indicated in Steps S4 and S6.

As described with reference to FIG. 2B, the power source 16 of the first patient monitor 10 is turned on and is providing power to the components of the first patient monitor 10. The power supply form the power source 16 may be "turned on" by establishing one or more connections from the power source 16 to a power bus that is connected to components of the first patient monitor 10 by, for example, closing one or more switches that routes power to the power bus. The power bus distributes the power from the power source 16, thereby fully turning on the first patient monitor 10. The coupling signal 32 activates the automatic power on circuit 36 and automatically controls the power state of the second patient monitor 7 without user intervention.

For example, upon the activation of the automatic power on circuit 36 in Step S3, if the second patient monitor 7 is off or in a sleep mode, the second patient monitor 7 is controlled by the automatic power on circuit 36 to automatically turn on so as to match the on state of the patient first monitor 10, as indicated in Steps S4 and S5. However, if the second patient monitor 7 is in an on state that already matches the on state of the first patient monitor 10, the second patient monitor 7 will remain in the same on state after activation of the automatic power on circuit, as indicated in Steps S4 and S6.

It is contemplated by the present disclosure that the automatic power on circuits 26, 36 described with reference to FIGS. 2A, 2B and 7 can be implemented individually or together in the first and second patient monitors 7, 10. Additionally, it is contemplated by the present disclosure that there can be multiple automatic power on circuits 26, 36 implemented in the first and second patient monitors 7, 10 such that each of the first and second patient monitors 7, 10 includes multiple infrared IR LEDs and multiple phototransistors. The automatic power on circuits 26, 36 described with reference to FIGS. 2A, 2B, and 7 are implemented in the first and second patient monitors 7, 10 to accomplish the following operations without any user intervention:

1) If the second patient monitor 7 is powered ON and positioned on, in, or proximate to a powered OFF first patient monitor 10, the first patient monitor 10 will automatically be powered ON;
2) If the second patient monitor 7 is powered ON and positioned on, in, or proximate to a powered ON first patient monitor 10, the first patient monitor 10 and the second monitor 7 will remain ON;
3) If the second patient monitor 7 is powered OFF and positioned on, in, or proximate to a powered ON first patient monitor 10, the second patient monitor 7 will automatically be powered ON;
4) If the second patient monitor 7 is powered OFF and positioned on, in, or proximate to a powered OFF first patient monitor 10, the first patient monitor 10 and the second monitor 7 will remain OFF (e.g., because the coupling signal will not be generated);
5) If the second patient monitor 7 is powered ON, and is placed in a separate monitor mount (e.g., not positioned on, in, or proximate to the first patient monitor 10), the second patient monitor 7 will remain ON;
6) If the second patient monitor 7 is powered OFF, and is placed in a separate monitor mount (e.g., not positioned on, in, or proximate to the first patient), the second patient monitor 7 will remain OFF (e.g., because the coupling signal will not be generated);
7) If the first patient monitor 10 is powered ON, and is placed in a separate monitor mount (e.g., not positioned on, in, or proximate to the second patient monitor), the first patient monitor 10 will remain ON; and
8) If the first patient monitor 10 is powered OFF, and is placed in a separate monitor mount (e.g., not positioned on, in, or proximate to the second patient), the first patient monitor 10 will remain OFF (e.g., because the coupling signal will not be generated).

In certain embodiments, the first patient monitor 10 or the second patient monitor 7 may employ a safety feature wherein the power OFF button needs to be depressed for a certain interval of time, such as without limitation five seconds or greater, to power OFF the device to avoid an inadvertent powering down of either or both monitors.

The automatic power on circuits 26, 36 described with reference to FIG. 2A, FIG. 2B and FIG. 7 provide improvements and advantages over prior art systems.

For example, when a patient is being transported between different patient care or hospital environments, clinicians are required to perform manual operations when transitioning between different medical devices (e.g., attaching cables or pushing of buttons on the front panel of a smaller transportable medical device or a larger stationary or portable medical device). This manual action increases workload on clinicians and increases the overall time for performing accurate patient assessment during transport of the patient between different patient care or hospital environments.

The automatic power on circuits 26, 36, described with reference to FIGS. 2A-7, allow for seamless and automatic control of the power states of medical devices in a way that reduces work load on clinicians and supports rapid patient assessment during the transport of patients between different patient care or hospital environments, which can be particularly advantageous when used in critical care environments where rapid assessment of a patient's condition is imperative.

Additional advantages of the automatic power on circuits 26, 36 described with reference to FIGS. 2A-7 of the present disclosure include overcoming the limitations of the smaller portable medical device in displaying information (e.g., physiological parameters) on a small-sized display. That is, the large-sized display of a larger stationary or portable medical device can be used to display information (e.g., patient data, medical history from EMR or other similar information) in various configurations that are easier for clinical providers to review without users' intervention to manually turn on/off the device. Furthermore, the larger medical device may be in communication with other medical devices (e.g., insulin pumps, or ventilators) such that more information can be displayed to clinical providers to review. The automatic power on circuit in accordance with the present disclosure may advantageously facilitate the continuous monitoring and information display on patient monitors wherever the patient being monitored is located (e.g., patient ward, ambulance, or operation room).

It should be understood by one of ordinary skill in the art that the present disclosure may be implemented by any combination of an apparatus, a system, an integrated circuit, and a computer program on a non-transitory computer readable recording medium. The one more processors 3, 12 may be implemented as an integrated circuit (IC), an application specific integrated circuit (ASIC), or large scale integrated circuit (LSI), system LSI, super LSI, or ultra LSI components which perform a part or all of the functions described in the present disclosure.

The present disclosure can include the use of computer programs or algorithms. The programs or algorithms can be stored on a non-transitory computer-readable medium for causing a computer, such as the one or more processors 3, 12, to execute the steps directed to the operation and control of the automatic power on circuit 26, 36 and the patient monitors 7, 10. For example, the one or more memories stores software or algorithms with executable instructions and the one or more processors 3, 12 can execute a set of instructions of the software or algorithms in association with the operation and control of the patient monitors The computer programs, which can also be referred to as programs, software, software applications, applications, components, or code, include machine instructions for a programmable processor, and can be implemented in a high-level procedural language, an object-oriented programming language, a functional programming language, a logical programming language, or an assembly language or machine language. The term computer-readable recording medium refers to any computer program product, apparatus or device, such as a magnetic disk, optical disk, solid-state storage device, memory, and programmable logic devices (PLDs), used to provide machine instructions or data to a programmable data processor, including a computer-readable recording medium that receives machine instructions as a computer-readable signal.

By way of example, a computer-readable medium can comprise DRAM, RAM, ROM, EEPROM, CD-ROM or other optical disk storage, magnetic disk storage or other magnetic storage devices, or any other medium that can be used to carry or store desired computer-readable program code in the form of instructions or data structures and that can be accessed by a general-purpose or special-purpose computer, or a general-purpose or special-purpose processor. Disk or disc, as used herein, include compact disc (CD), laser disc, optical disc, digital versatile disc (DVD), floppy disk and Blu-ray disc where disks usually reproduce data magnetically, while discs reproduce data optically with lasers. Combinations of the above are also included within the scope of computer-readable media.

Use of the phrases "capable of," "capable to," "operable to," or "configured to" in one or more embodiments, refers to some apparatus, logic, hardware, and/or element designed in such a way to enable use of the apparatus, logic, hardware, and/or element in a specified manner. The subject matter of the present disclosure is provided as examples of apparatus, systems, methods, circuit, and programs for performing the features described in the present disclosure. However, further features or variations are contemplated in addition to the features described above. It is contemplated that the implementation of the components and functions of the present disclosure can be done with any newly arising technology that may replace any of the above implemented technologies.

Additionally, the above description provides examples, and is not limiting of the scope, applicability, or configuration set forth in the claims. Changes may be made in the function and arrangement of elements discussed without departing from the spirit and scope of the disclosure. Various embodiments may omit, substitute, or add various procedures or components as appropriate. For instance, features described with respect to certain embodiments may be combined in other embodiments.

Various modifications to the disclosure will be readily apparent to those skilled in the art, and the generic principles defined herein may be applied to other variations without departing from the spirit or scope of the present disclosure. Throughout the present disclosure the terms "example," "examples," or "example" indicate examples or instances and do not imply or require any preference for the noted examples. Thus, the present disclosure is not to be limited to the examples and designs described herein but is to be accorded the widest scope consistent with the principles and novel features disclosed.

The invention claimed is:

1. An automatic power on system, comprising:
a first electronic device including:
a mounting area; and
a first portion of an automatic power on circuit; and
a second electronic device including:
a housing configured to enable the second electronic device to be positioned on, in, or proximate to the mounting area of the first electronic device; and
a second portion of the automatic power on circuit;
wherein when the second electronic device is positioned on, in, or proximate to the mounting area of the first electronic device, the automatic power on circuit is configured to:
establish a coupling signal between the first portion of the automatic power on circuit and the second portion of the automatic power on circuit,
activate the automatic power on circuit based on the coupling signal, and
automatically control an on/off state of the first electronic device or the second electronic device based on the activation of the automatic power on circuit;
wherein the automatic power on circuit includes a detection circuit,
wherein the second portion of the automatic power on circuit includes a transmitting circuit that generates the coupling signal, and
wherein the first portion of the automatic power on circuit includes a receiving circuit that generates an electrical signal in response to receiving the coupling signal.

2. The automatic power on system of claim 1, wherein the mounting area includes a cavity or opening and the second electronic device is configured to be slid into the cavity or opening of the mounting area of the first electronic device.

3. The automatic power on system of claim 1, wherein when the first electronic device is in an on/off state that matches the on/off state of the second electronic device prior to activation of the automatic power on circuit, the first electronic device is controlled to remain in a same on/off state after activation of the automatic power on circuit.

4. The automatic power on system 1, wherein upon the activation of the automatic power on circuit, the second electronic device is controlled to turn on so as to match an on state of the first electronic device.

5. The automatic power on system of claim 1, wherein when the second electronic device is in an on/off state that matches the on/off state of the first electronic device prior to activation of the automatic power on circuit, the second electronic device is controlled to remain in a same on/off state after activation of the automatic power on circuit.

6. The automatic power on system of claim 1, wherein the detection circuit is a photodetector circuit,
the transmitting circuit includes a light transmitting circuit with a light source that generates light as the coupling signal, and

the receiving circuit includes a light receiving circuit with a photodetector that generates an electrical signal in response to receiving the coupling signal.

7. The automatic power on system of claim 6, wherein the first electronic device further includes a first area configured to pass the coupling signal transmitted from the transmitting circuit of the second electronic device to the receiving circuit of the first electronic device.

8. The automatic power on system of claim 7, wherein the second electronic device further includes a second area configured to pass the coupling signal transmitted from the transmitting circuit to the first electronic device.

9. The automatic power on system of claim 8, wherein the first area and the second area are aligned when the second electronic device is positioned on, in, or proximate to the mounting area of the first electronic device.

10. The automatic power on system of claim 1, wherein upon the activation of the automatic power on circuit, the first electronic device is controlled to turn on so as to match an on state of the second electronic device.

11. An automatic power on circuit, comprising:
a first portion of the automatic power on circuit arranged within a first electronic device; and
a second portion of the automatic power on circuit arranged within a second electronic device, the second electronic device having a housing configured to be positioned on, in, or proximate to a mounting area of the first electronic device the mounting area comprising a cavity configured to receive the second electronic device,
wherein when the second electronic device is positioned on, in, or proximate to the mounting area of the first electronic device, the automatic power on circuit is configured to:
establish a coupling signal between the first portion of the automatic power on circuit and the second portion of the automatic power on circuit,
activate the automatic power on circuit based on the coupling signal, and
automatically control an on/off state of the first electronic device or the second electronic device based on the activation of the automatic power on circuit.

12. The automatic power on circuit of claim 11, wherein upon the activation of the automatic power on circuit, the first electronic device is controlled to turn on so as to match an on state of the second electronic device.

13. The automatic power on circuit of claim 11, wherein when the first electronic device is in an on/off state that matches the on/off state of the second electronic device prior to activation of the automatic power on circuit, the first electronic device is controlled to remain in a same on/off state after activation of the automatic power on circuit.

14. The automatic power on circuit 11, wherein
upon the activation of the automatic power on circuit, the second electronic device is controlled to turn on so as to match an on state of the first electronic device.

15. The automatic power on circuit of claim 11, wherein when the second electronic device is in an on/off state that matches the on/off state of the first electronic device prior to activation of the automatic power on circuit, the second electronic device is controlled to remain in a same on/off state after activation of the automatic power on circuit.

16. The automatic power on circuit of claim 11, wherein
the automatic power on circuit is a photodetector circuit,
the second portion of the automatic power on circuit includes an infrared (IR) transmitting circuit with an IR light source, and
the first portion of the automatic power on circuit includes an IR receiving circuit with a photodetector.

17. The automatic power on circuit of claim 11, wherein
the automatic power on circuit is a photodetector circuit,
the first portion of the automatic power on circuit includes an infrared (IR) transmitting circuit with an IR light source, and
the second portion of the automatic power on circuit includes an IR receiving circuit with a photodetector.

18. A first electronic device for wirelessly coupling with a second electronic device having a first portion of an automatic on/off circuit, the first electronic device comprising:
a housing configured to be positioned on, in, or proximate to a mounting area of the second electronic device the mounting area comprising a cavity configured to receive the first electronic device;
a second portion of the automatic on/off circuit; and
when the first electronic device is positioned on, in, or proximate to the mounting area of the second electronic device, the second portion of the automatic power on circuit is configured to:
establish a coupling signal between the second portion of the automatic power on circuit and the first portion of the automatic power on circuit,
activate the automatic power on circuit based on the coupling signal, and
automatically control an on/off state of the second electronic device based on the activation of the automatic power on circuit.

19. The automatic power on system of claim 1, wherein the mounting area is arranged at a back surface of the first electronic device.

* * * * *